United States Patent [19]

Hughes et al.

[11] 4,105,790
[45] Aug. 8, 1978

[54] α-AMINO KETONE DERIVATIVES

[75] Inventors: Clifford Ronald Hughes; Stephen John Jackson; John Preston; Peter Leslie Walton, all of Macclesfield, England

[73] Assignee: Imperial Chemical Industries Limited, London, England

[21] Appl. No.: 740,195

[22] Filed: Nov. 9, 1976

[30] Foreign Application Priority Data

Nov. 25, 1975 [GB] United Kingdom ............... 48402/75

[51] Int. Cl.$^2$ ..................... A61K 31/24; C07C 101/04
[52] U.S. Cl. ..................................... 424/309; 424/319; 260/144; 260/307 R; 260/349; 260/516; 260/519; 260/558 A; 560/12; 560/17; 560/29; 560/42; 544/162; 544/159; 544/174; 544/176; 544/137; 544/157; 544/168; 544/171
[58] Field of Search ............ 260/471 R, 519; 560/42; 424/309, 319

[56] References Cited

U.S. PATENT DOCUMENTS 3,914,286  10/1975  Mieville ......................... 260/471 R

OTHER PUBLICATIONS

Niederl et al., J. of Organic Chem. 1952, 11, 1617–1620.
Gorini et al., Chem. Abst. 3399(a), vol. 60, 1964.
Valcavi, Chem. Absts. 6778(g), vol. 60, 1964.
Wolff et al., Chem. Absts. 31318(g), vol. 82, 1975.

*Primary Examiner*—James O. Thomas, Jr.
*Assistant Examiner*—G. T. Breitenstein
*Attorney, Agent, or Firm*—Cushman, Darby & Cushman

[57] ABSTRACT

The invention concerns α-aminoacyl derivatives of phenyl-, phenoxy-, thiophenoxy- and phenylsulphinylalkanoic acids together with their amides, esters and pharmaceutically acceptable salts; processes for their preparation; and pharmaceutical compositions for therapeutic use in inhibiting the formation of thrombi and also in reducing the persistence of thrombi formed in the blood of warm blooded animals. Representative compounds of the invention are methyl 4-(aminoacetyl)phenoxyacetate, 4-(aminoacetyl)phenoxyacetic acid and methyl 4-(aminoacetyl)-thiophenoxyacetate, preferably as their hydrochlorides.

7 Claims, No Drawings

α-AMINO KETONE DERIVATIVES

This invention relates to amines and in particular it relates to α-aminoketone derivatives which possess the property of inhibiting the formation of insoluble fibrin from fibrin.

According to the invention there is provided an α-aminoketone derivative of the formula:

     I wherein $R^1$ is hydrogen, a formyl radical or a ($C_{1-4}$-alkoxy)-carbonyl radical; $R^2$ is hydrogen, a $C_{1-4}$-alkyl radical or a ($C_{1-4}$-alkoxy)carbonyl radical; $R^3$ is a hydroxy or $C_{1-8}$-alkoxy radical or a radical of the formula $-NR^4R^5$ wherein $R^4$ is hydrogen or a $C_{1-4}$-alkyl radical, and $R^5$ is hydrogen or a $C_{1-4}$-alkyl radical optionally bearing a ($C_{1-4}$-alkoxy)carbonyl radical as a substituent or $R^4$ and $R^5$ together form a 5-or 6-membered heterocyclic radical which optionally includes an oxygen atom as an additional hetero-atom; and wherein Ar is a m- or p-phenylene radical optionally bearing a $C_{1-4}$-alkoxy radical as a substituent; X is oxygen, sulphur, a sulphinyl (O=S<) radical, or a direct link between Ar and A; and A is a straight- or branched-chain $C_{1-6}$-alkylene radical optionally bearing a ($C_{1-4}$-alkoxy)carbonyl radical as a substituent; or a pharmaceutically acceptable acid addition salt or a metal salt complex thereof of an α-aminoketone derivative of formula I wherein $R^1$ is hydrogen; or a pharmaceutically acceptable base addition salt of an α-aminoketone derivative of formula I wherein $R^3$ is a hydroxy radical.

It will be observed that those compounds of formula I wherein $R^2$ is other than hydrogen or wherein A is other than a symmetrical $C_{1-6}$-alkylene radical contain an asymmetrically substituted carbon atom, and that accordingly, such compounds, and similarly compounds of formula I wherein $R^3$ is a substituent containing an asymmetrically substituted carbon, may be isolated in racemic and optically active forms. This specification is to be understood as addressed to the racemic form of such compounds of formula I containing one or more asymmetrically substituted carbon atoms, and to any optical isomer which shows the above mentioned useful property; it being well known in the general chemotherapeutic art how to resolve racemic forms and to determine the biological properties of the individual optical isomers.

A particularly suitable value for $R^1$ or $R^2$ when it is a ($C_{1-4}$-alkoxy)carbonyl radical is, for example, an ethoxy- or methoxy-carbonyl radical.

A particularly suitable value for $R^2$ when it is a $C_{1-4}$-alkyl radical is, for example, an ethyl radical.

A particularly suitable value for $R^3$ when it is a $C_{1-8}$-alkoxy radical is, for example, a methoxy, ethoxy, n-propoxy, isopropoxy, n-butoxy or n-hexyloxy radical.

A particularly suitable value for $R^4$ or $R^5$ when it is a $C_{1-4}$-alkyl radical is, for example, a methyl or ethyl radical.

A particularly suitable value for a ($C_{1-4}$-alkoxy)-carbonyl radical when present as an optional substituent on $R^5$ or A is for example a methoxy or ethoxy-carbonyl radical.

A particularly suitable value for the heterocyclic radical formed from $R^4$, $R^5$ and the adjacent nitrogen atom is, for example, a morpholine radical.

A particularly suitable value for $R^5$ when it is a $C_{1-4}$-alkyl radical bearing a ($C_{1-4}$-alkoxy)carbonyl radical as a substituent is, for example, a $C_{1-4}$-alkyl radical bearing an α-($C_{1-4}$-alkoxy)carbonyl radical, for example a methyl, ethyl or propyl radical bearing an α-methoxycarbonyl or α-ethoxycarbonyl radical.

A particularly suitable value for $R^3$ when it is a radical of the formula $-NR^4R^5$ is, for example, an amino, $C_{1-4}$-alkylamino, for example methylamino, di-($C_{1-4}$-alkyl)amino, for example diethylamino, α-($C_{1-4}$-alkoxy)-carbonyl-$C_{1-4}$-alkylamino, for example α-(methoxycarbonyl)ethylamino, or a morpholino radical.

A particularly suitable value for a $C_{1-4}$-alkoxy radical when present as a substituent on a m- or p-phenylene radical is, for example, a methoxy radical.

A particularly suitable value for A when it is a straight or branched chain $C_{1-6}$-alkylene radical is, for example, a methylene, ethylene or propylene radical or a radical of the formula $-CH(CH_3)-$ or $-C(CH_3)_2-$; and a particularly suitable value for A when it is a straight or branched chain $C_{1-6}$-alkylene radical bearing a ($C_{1-4}$-alkoxy)-carbonyl radical as a substituent is, for example, a methoxycarbonylmethylene or an ethoxycarbonylmethylene radical.

A particularly suitable pharmaceutically acceptable acid addition salt is, for example, a hydrohalide, for example a hydrochloride or hydrobromide, a sulphate, phosphate or 2-hydroxyethylsulphonate salt, or a salt with a carboxylic acid, for example, a citrate, lactate or acetate salt.

A particularly suitable pharmaceutically acceptable metal salt complex of an acid addition salt is, for example, a complex with a zinc or iron salt, for example with zinc chloride or ferric chloride.

A particularly suitable base addition salt is for example, an alkali metal or alkaline earth metal salt, for example a sodium, potassium or calcium salt, an aluminium salt, or a salt of an organic base affording a pharmaceutically acceptable cation, for example triethanolamine.

A particular group of compounds of the invention comprises those compounds of formula I wherein $R^2$ is hydrogen, Ar is a p-phenylene radical, and A is a methylene radical, together with their pharmaceutically acceptable salts as defined hereinbefore.

Within this particular group a first preferred group of compounds are those wherein X is oxygen, together with the pharmaceutically acceptable salts thereof as defined hereinbefore; and a second preferred group of compounds are those wherein X is sulphur or a sulphinyl (O=S<) radical, together with the pharmaceutically acceptable salts thereof as defined hereinbefore.

A yet further particular group of compounds of the invention comprises those compounds of formula I, wherein $R^2$ is hydrogen, Ar is a p-phenylene radical, and X is a direct link between Ar and the radical A, together with their pharmaceutically acceptable salts as defined hereinbefore.

In each of the above groups $R^3$ may be as stated above but particularly preferred values for $R^3$ are a hydroxy, methoxy or α-(methoxycarbonyl)ethylamino radical. In addition in each of the above groups a particularly preferred salt of a compound of formula I wherein $R^1$ is hydrogen is for example, an acid addition salt, for example a hydrochloride.

Specific α-aminoketone derivatives of the invention are described in the accompanying Examples and of these the following compounds are of particular interest:

4-(aminoacetyl)phenoxyacetic acid, methyl 4-(aminoacetyl)phenoxyacetate, methyl 4-(aminoacetyl)thiophenoxyacetate, methyl 4-[N-(formyl)aminoacetyl]phenoxyacetate, methyl 4-[N-(formyl)aminoacetyl]thiophenoxyacetate, methyl 4-[N-(formyl)aminoacetyl]phenylsulphinylacetate and N-{3-[4-(aminoacetyl)phenyl]propionyl}alanine methyl ester, and the pharmaceutically acceptable salts thereof as defined hereinbefore, especially the acid-addition salts thereof.

The α-amino-ketone derivatives of formula I may be made by processes which are applicable to the manufacture of analogous compounds. Such processes are exemplified by the following which are provided as further features of the invention, and in which $R^1$, $R^2$, $R^3$, $R^4$, $R^5$, Ar, X and A have the meanings stated above:

(a) For a compound of formula I wherein $R^1$ is hydrogen reducing a compound of the formula:

$$B.CO.Ar.X.A.CO.R^3 \qquad II$$

wherein B is an azidoalkyl radical of the formula $N_3.CHR^2-$, a nitroalkyl radical of the formula $NO_2.CHR^2-$, a diazoalkyl radical of the formula $N_2{:}CR^2-$ or a hydroxyiminoalkyl radical of the formula $HO.N{=}CR^2-$.

The reduction may be conveniently carried out, for example, directly with hydrogen, by using a palladium or platinum-on-charcoal catalyst in a solvent or diluent, for example water or a $C_{1-3}$-alkanol such as ethanol, or in a mixture thereof. The reduction is also conveniently carried out in the presence of an acid, for example an inorganic acid, for example hydrochloric or sulphuric acid, or an organic acid, for example citric, lactic or acetic acid, and in which case an acid addition salt of a compound of formula I wherein $R^1$ is hydrogen may be isolated from the reduction. The reduction may be carried out at, for example, ambient temperature and atmospheric pressure and is continued until the uptake of hydrogen indicates that reduction of the α-carbonyl group is beginning to occur.

Alternatively, the reduction may be conveniently carried out, for example, using a reducing metal, for example, zinc or iron, preferably in powdered form, in a solvent or diluent, for example ethanol or methanol, in the presence of an acid, for example hydrochloric or acetic acid. The reaction is normally exothermic and is conveniently carried out at 25° to 60° C. The product of formula I may conveniently be isolated from the reaction as the zinc or iron complex of its acid addition salt with the acid used in the reduction.

Also when a compound of formula II wherein B is an azidoalkyl radical of the formula $N_3.CHR^2-$ is to be reduced, the reduction may be conveniently carried out indirectly in two steps by reaction with triphenyl phosphine to form a phosphazo intermediate of the formula:

$$Ph_3P{=}N.CHR^2.CO.Ar.X.A.CO.R^3 \qquad III$$

followed by acid hydrolysis of the phosphazo intermediate III. Each of the two steps may be carried out in an inert solvent for example tetrahydrofuran and at a temperature of 20°–60° C., and the steps are conveniently performed in the same reaction vessel. (b) For a compound of formula I wherein $R^3$ is a $C_{1-8}$-alkoxy radical esterifying a carboxylic acid of the formula:

$$R^1NH.CHR^2.CO.Ar.X.A.CO_2H \qquad IV$$

or a reactive derivative thereof, by reaction with a $C_{1-8}$-alkanol or a diazo-$C_{1-8}$-alkane.

A particularly suitable $C_{1-8}$-alkanol is for example methanol, ethanol, n-propyl, i-propyl, n-butyl, or n-hexyl alcohol; and a particularly suitable diazo-$C_{1-8}$-alkane is, for example, diazomethane or diazoethane.

The esterification may be carried out by any known esterification procedure which is compatible with the other remaining substituents present on a particular compound of formula I. Thus, for example, a carboxylic acid of formula IV may be reacted with an excess of a $C_{1-8}$-alkanol in the presence of acid, for example hydrochloric acid, at a temperature of, for example, 30° to 100° C. to give a compound of formula I wherein $R^1$ is hydrogen and $R^3$ is a $C_{1-8}$-alkoxy radical, it being understood that an N-formyl or an N-($C_{1-4}$-alkoxy)carbonyl radical present in the starting material of formula IV is removed under these conditions.

The esterification may also be carried out by reacting an acid of formula IV with a $C_{1-8}$-alkanol in the presence of a condensing agent for example, dicyclohexylcarbodiimide or a mixture of triphenylphosphine and diethyl azodicarboxylate, conveniently in an inert solvent for example tetrahydrofuran and at ambient temperature. This procedure is particularly preferred for the preparation of esters from acids of formula IV wherein $R^1$ is other than hydrogen.

The esterification may also be carried out by reacting a reactive derivative of an acid of formula IV with a $C_{1-8}$-alkanol. Particularly suitable reactive derivatives are, for example, the acid halides, for example the acid chloride, acid azide, acid anhydride or the mixed anhydride with a $C_{1-4}$-alkanoic acid, for example with formic acid, of the acid of formula IV. The reaction is conveniently carried out in the presence of an inert solvent or diluent, for example tetra hydrofuran or diethyl ether, and may be accelerated by heating, for example, at the reflux temperature of the reaction mixture. The reactive derivatives of the acids of formula IV are conveniently obtained in situ by conventional procedures immediately prior to the esterification.

The esterification may also be carried out by reacting a carboxylic acid of formula IV with a diazo-$C_{1-8}$-alkane at or near ambient temperature and conveniently, using an excess of diazo-$C_{1-8}$-alkane in an inert diluent or solvent, for example diethyl ether. This procedure is particularly suitable for the preparation of the methyl and ethyl esters of carboxylic acids of formula IV.

It is also to be understood that the esterification may be performed in two steps. Thus, in the first step a reactive ester, for example the methyl or ethyl ester of a compound of formula IV, is formed by any of the above procedures, and in the second step, such a reactive methyl or ethyl ester is reacted with a large excess of a $C_{1-8}$-alkanol other than methanol or ethanol respectively, in the presence of acid, for example hydrochloric acid, and conveniently at an elevated temperature, for example at the reflux temperature of the reaction mixture. This procedure is known as transesterification and for the reasons stated above is only applicable to the preparation of compounds of formula I wherein $R^1$ is hydrogen and $R^3$ is a $C_{1-8}$-alkoxy radical. It is also to be understood that a ($C_{1-4}$-alkoxy)-carbonyl radical when present as a value for $R^2$ will also undergo transesterification at the same time.

(c) For a compound of formula I wherein $R^3$ is a radical of the formula $-NR^4R^5$, reacting a carboxylic acid of formula IV or a reactive derivative thereof, with an amine of the formula $HNR^4R^5$.

The reaction may be carried out by any method known for the formation of amido linkages which is compatible with the other remaining substituents present on the particular compound of formula I required.

Thus, for example, the reaction with the amine of the formula $HNR^4R^5$ may be carried out in the presence of similar condensing agents, for example dicyclohexylcarbodiimide, and under essentially similar conditions as those specified hereinabove in process (b). This procedure is particularly preferred for the preparation of compounds of formula I wherein $R^1$ is other than hydrogen and $R^3$ is a radical of the formula $-NR^4R^5$.

Alternatively the reaction with the amine may be carried out using, for example, such reactive derivatives of an acid of formula IV, and such general conditions as are specified hereinabove for process (b); and when a compound of formula I wherein $R^1$ is hydrogen and $R^3$ is a radical of the formula $-NR^4R^5$ is required the starting acid of formula IV is preferably used as its acid addition salt.

(d) For a compound of formula I wherein $R^1$ is hydrogen, reacting a halogeno compound of the formula:

Q.CHR².CO.Ar.X.A.CO.R³    V wherein Q is a halogen atom, for example a chlorine, bromine or iodine atom, with hexamine (hexamethylenetetramine) followed by acidic hydrolysis of the thus formed hexamine adduct.

The reaction with hexamine is conveniently carried out, for example, using equimolar amounts of reactants in an inert solvent or diluent, for example, ether, tetrahydrofuran or chloroform and at a temperature of, for example 20°–60° C., for example at or near ambient temperature.

The acidic hydrolysis of the intermediate hexamine adduct with the compound of formula V is conveniently carried out as a separate step in an inert solvent or diluent, for example ethanol, and at a temperature of for example, 40°–100° C. A particularly suitable acid for use in the hydrolysis is, for example, hydrochloric acid, and the compound of formula I wherein $R^1$ is hydrogen is conveniently isolated from the reaction mixture as the acid addition salt of the acid used in the hydrolysis.

(e) For a compound of formula I wherein $R^1$ is a formyl or ($C_{1-4}$-alkoxy)carbonyl radical, reacting an amino compound of the formula:

H₂N.CHR².CO.Ar.X.A.CO.R³    VI with an acylating agent derived structurally from an acid of the formula $R^6.CO_2H$ wherein $R^6$ is hydrogen or a $C_{1-4}$-alkoxy radical.

A particularly suitable acylating agent derived structurally from the above-mentioned acid is, for example, an acid halide, for example an acid chloride and in the case of formyl chloride this may conveniently be obtained in situ by passing carbon monoxide and hydrogen chloride into the reaction mixture.

Alternatively when a compound of formula I wherein $R^1$ is a formyl radical is required, a particularly suitable acylating agent is, for example, the mixed anhydride of formic and acetic acid which is conveniently formed in situ from formic acid and acetic anhydride in the reaction mixture; or a tri-($C_{1-4}$-alkyl)orthoformate for example trimethylorthoformate.

The acylation reaction is preferably carried out in an inert, essentially dry solvent or diluent, for example, diethyl ether, chloroform, tetrahydrofuran or methylene chloride, and conveniently at a temperature of, for example, 0°–100° C. except where formyl chloride is used when a temperature of −20° to +20° C. may be used. A weak base, for example pyridine or 2,6-lutidine, may also be present and may be used in excess, for example as solvent.

(f) For a compound of formula I wherein $R^2$ is other than a ($C_{1-4}$-alkoxy)carbonyl radical and $R^3$ is a hydroxy radical, hydrolysing an ester of the formula:

R¹NH.CHR⁷.CO.Ar.X.A.CO.R⁸    VII wherein $R^7$ is hydrogen or a $C_{1-4}$-alkyl radical and $R^8$ is a $C_{1-8}$-alkoxy, benzyloxy or phenoxy radical.

The hydrolysis may be carried out under aqueous acidic or basic conditions. Acidic conditions are preferred when a compound of formula I, wherein $R^1$ is hydrogen and $R^3$ is a hydroxy radical, is required, and the product may conveniently be isolated as the acid addition salt of the acid used in the hydrolysis. It is to be understood that N-formyl or N-($C_{1-4}$-alkoxy)carbonyl groups present as $R^1$ in the starting esters of formula VII are also removed by aqueous acidic hydrolysis.

Basic conditions are preferred when a compound of formula I, wherein $R^1$ is other than hydrogen and $R^3$ is a hydroxy radical, is required, and an especially labile ester, for example an ester of formula VII wherein $R^8$ is a phenoxy radical must be used to prevent concomitant removal of the $R^1$ substituent.

The hydrolysis is preferably carried out in a water miscible solvent, for example an alcohol, for example ethanol, and at a temperature of, for example, 0°–100° C., higher temperatures generally being employed for the acidic hydrolysis than for the basic hydrolysis.

(g) For a compound of formula I wherein $R^1$ is hydrogen, reacting an oxazole of the formula:

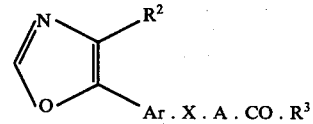

VIII with an inorganic acid.

A particularly suitable inorganic acid is for example, a hydrogen halide, for example hydrogen chloride or hydrogen bromide. The reaction with inorganic acid is conveniently carried out in a solvent or diluent, for example a $C_{1-8}$-alkanol, for example methanol or ethanol at a temperature of, for example, 40°–150° C. It is to be understood that when the oxazole of formula VIII contains an ester function, it is necessary to use the corresponding $C_{1-8}$-alkanol as solvent or diluent, if transesterification is to be prevented. Equally if hydrolysis of the ester function of such an oxazole of formula VIII is to be avoided, it is necessary to carry out the reaction under essentially anhydrous conditions.

(h) For a compound of formula I wherein $R^1$ is hydrogen, deacylating a compound of the formula:

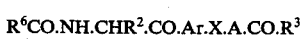
R⁶CO.NH.CHR².CO.Ar.X.A.CO.R³    IX wherein $R^6$ is hydrogen or a $C_{1-4}$-alkoxy radical.

The deacylation is conveniently carried out in, for example, an alcohol solvent, for example methanol or ethanol, and in the presence of an inorganic acid for example hydrogen chloride, and at a temperature of, for example, 10°–100° C., but preferably at or near ambient temperature. It will be appreciated that unless essentially anhydrous conditions are used hydrolysis of any ester function in the starting material of formula IX will also occur. Aqueous acidic conditions are particularly suitable when a compound of formula I wherein $R^1$ is hydrogen, $R^2$ is other than a ($C_{1-4}$-alkoxy)carbonyl radical and $R^3$ is a hydroxy radical is required.

The product of formula I wherein $R^1$ is hydrogen may conveniently be isolated from the reaction mixture as the acid addition salt with the acid used in the reaction.

(i) For a compound of formula I wherein X is a sulphinyl (O=S<) radical, oxidising a compound of formula I wherein X is sulphur or, for a compound of formula I wherein $R^1$ is hydrogen, an acid addition salt thereof.

The oxidation is conveniently carried out in an inert solvent or diluent, for example ethanol or methanol, or an aqueous mixture thereof, and, for example, at or near ambient temperature. A particularly convenient oxidant is, for example, sodium metaperiodate, mercuric oxide, or hydrogen peroxide, and the oxident is conveniently used in equimolar quantity to that of the starting thio compound. When the required product is a compound of formula I wherein $R^1$ is hydrogen and X is a sulphinyl radical the amino starting material is preferably used as its acid addition salt, for example, its hydrochloride.

(j) Oxidising a compound of the formula:

   X or for a compound of formula I wherein $R^1$ is hydrogen, an acid addition salt thereof.

A particularly suitable oxidising agent is, for example, dimethyl sulphoxide especially in conjunction with acetic anhydride or dicyclohexylcarbodiimide, and the oxidation is conveniently carried out in an inert diluent or solvent, for example tetrahydrofuran or acetonitrile, or in an excess of the oxidant, especially when dimethyl sulphoxide is used. When a compound of formula I wherein $R^1$ is hydrogen is required, the oxidation is preferably carried out on the appropriate acid addition salt, for example, the hydrochloride of the starting material of formula X.

Alternatively when $R^1$ is other than hydrogen the oxidation may be carried out by Oppenauer oxidation, for example, by refluxing a compound of formula X, wherein $R^1$ is other than hydrogen, with an excess of acetone in the presence of a catalytic amount of an aluminium $C_{1-4}$-alkoxide, for example an aluminium propoxide.

(k) For a compound of formula I wherein $R^1$ is hydrogen, hydrolysing a compound of the formula:

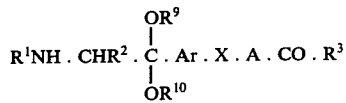   XI wherein $R^9$ is hydrogen or a $C_{1-4}$-alkyl radical, for example a methyl or ethyl radical, and $R^{10}$ is a $C_{1-4}$-alkyl radical, for example a methyl or ethyl radical, or $R^9$ and $R^{10}$ together form a straight- or branched chain- $C_{2-6}$- alkylene radical, for example an ethylene or 2,2-dimethyl-1,3-propylene radical.

The hydrolysis is preferably carried out under aqueous acidic conditions, for example in the presence of a mineral acid, for example hydrogen chloride. A solvent or diluent, for example, ethanol, methanol or tetrahydrofuran, may conveniently be used. The hydrolysis is preferably performed at or near room temperature, and in any case under mild conditions such that ester groups when present in the starting material of formula XI are not also hydrolysed. It is to be understood, however, that N-formyl or N-($C_{1-4}$-alkoxy)carbonyl groups present in the starting material of formula XI are hydrolysed during process (k).

The starting materials are all obtainable using well known procedures applicable to the synthesis of analogous compounds. Thus, the starting materials of formula II are readily obtained from the compounds of formula V by reaction of the compound of formula V with sodium azide (to give a compound II wherein B is a radical of the formula $N_3.CHR^2$—), or a metal nitrite, for example silver nitrite (to give a compound II wherein B is a radical of the formula $NO_2.CHR^2$—); from the corresponding benzoyl chloride derivative by reaction with the appropriate diazoalkane (to give a compound II wherein B is a radical of the formula $N_2:CR^2$—); or from the corresponding alkyl phenylketone derivative by reaction with amyl nitrite (to give a compound II wherein B is a radical of the formula $HO.N=CR^2$—).

The starting materials of formula V are themselves obtained from an aromatic compound of the formula:

   XII by a Friedel-Craft reaction using a haloacyl halide for example chloroacetyl chloride, or an acyl halide followed by direct halogenation. The benzoyl chloride derivatives corresponding to the starting materials of formula V are prepared from the benzoic acids of the formula:

$HO_2C.Ar.X.A.CO.R^3$   XIII by reaction with a chlorinating agent, for example thionyl chloride or pivaloyl chloride. The benzoic acids of formula XIII are themselves obtainable by reaction of the corresponding phenol or thiophenol carboxylic acid with the appropriate haloalkanoic acid derivative. The alkylphenyl ketones corresponding to the starting materials of formula V, are themselves obtained by Friedel-Craft acylation of an aromatic compound of formula XII.

Those starting materials of formula VII wherein $R^8$ is a phenoxy or benzyloxy radical may be made by an analogous esterification procedure to that described in process (b).

Those starting oxazoles of formula VIII wherein $R^2$ is other than hydrogen are obtained by reaction of the appropriate isonitrile of the formula $CN.CH_2R^2$ with the corresponding chloride derived from benzoic acid of formula XIII. The remaining oxazole starting materials of formula VIII wherein $R^2$ is hydrogen may be obtained by any appropriate general method of oxazole synthesis, for example, as described by Turchi and Dewar (Chemical Reviews, 1975, 75, 389).

The starting materials of formula X may be obtained by reaction of the appropriate phenol or thiophenol derivative of the formula:

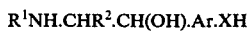   XIV with the corresponding haloalkanoic acid derivative. The derivatives of formula XIV are themselves obtained by reduction of the corresponding (aminoacyl)-phenol or thiophenol derivative in conventional manner, for example, as described by Howe et alia, in J. Medicinal Chemistry, 1968, 11, 1000.

The starting materials of formula XI will be recognised as acetals ($R^9$ is hydrogen) or ketals ($R^9$ is other than hydrogen) of the compounds of the invention and may be made by direct acid catalysed reaction of a compound of formula I (and in the case where $R^1$ is hydrogen, as their acid addition salts) with the appropriate alcohol. Alternatively the acetal or ketal function may be incorporated at an earlier stage in one of the above synthetic sequences.

The compounds of formula I wherein $R^1$ is hydrogen may be converted into pharmaceutically acceptable acid addition salts or a metal salt complex thereof as defined hereinabove by reaction with a suitable acid and optionally thereafter with a suitable metal salt using conventional means which are compatible with the remaining substituents. Similarly compounds of formula I wherein $R^3$ is a hydroxyl radical may be converted into pharmaceutically acceptable base addition salts as defined hereinabove by reaction with a suitable base using conventional means which are compatible with the remaining substituents.

As indicated above, the α-aminoketone derivatives of the invention possess the property of inhibiting the formation of insoluble fibrin from fibrin. Thrombus formation or clotting in blood plasma is a complex process, but the final stages of this process involve the linking together of fibrin units to form a fully ligated thrombus under the catalytic control of the enzyme fibrinoligase (Factor XIIIa). While the thrombus still consists of distinct fibrin units, it can be readily and reversibly dispersed by a 1% w/v aqueous solution of monochloracetic acid, but once fully ligated, the thrombus is insoluble in this monochloracetic acid solution.

The property of inhibiting the formation of insoluble fibrin possessed by the α-aminoketone derivatives of the invention can be demonstrated in vitro by measuring the effect of a test compound on the solubility of fibrin clots in 1% w/v aqueous monochloracetic acid solution. The fibrin clots are obtained by adding bovine thrombin to an aqueous buffered solution of radiolabelled ($^{125}I$) human fibrinogen which contains physiologically effective amounts of the enzyme fibrinoligase. In this test the compounds of the invention all show increased solubility of the fibrin clots at a concentration of 500 p.p.m. or less.

The property of inhibiting the formation of insoluble fibrin possessed by the α-aminoketone derivatives of the invention has also been demonstrated by administering a test compound to a rabbit and then measuring the solubility in 1% w/v aqueous monochloracetic acid solution of the fibrin clots formed by recalcification of samples of the rabbit's blood plasma taken at intervals after administration of the test compound. In this test, the compounds of the invention increased the solubility of the fibrin clots formed when administered at a dose of 100mg./kg. or less without any symptoms of toxicity being observed. In particular, methyl 4-(aminoacetyl)-phenoxyacetate shows activity on oral administration, and plasma samples taken up to 24 hours after dosing produce fibrin clots which are soluble in 1% w/v aqueous monochloroacetic acid solution.

The α-aminoketone derivatives of the invention thus possess the property of inhibiting the formation of a fully ligated fibrin clot. This property is important in the physiology of thrombus formation in vivo because it means that a thrombus formed in the presence of an α-aminoketone derivative of the invention will be more susceptible to dissolution by the protease occurring naturally in blood and so the α-aminoketone derivatives are useful for inhibiting the formation of thrombi and also reducing the persistence of thrombi formed in the blood of warm blooded animals.

The property of the α-aminoketone derivatives of inhibiting the formation of insoluble fibrin is also important in other physiological processes which involve the deposition of ligated fibrin, since inhibition of such a process can be used to produce a therapeutic effect. Thus, for example, in those tumours which require a fibrin network for maintenance, invasion of other tissues, spread or the establishment of metastases, the α-aminoketone derivatives of the invention are capable of limiting the disease process when used along or in conjunction with cytotoxic agents, antimetabolites or immune potentiators. This use of the α-aminoketone derivatives is demonstrated by the effect of the compounds in limiting the spread and growth of chemically induced or transplanted tumours in immunologically deprived or normal rodents or in limiting the formation or establishment of tumour emboli or metastases in the ear chamber of rabbits injected with a transplantable metastasing tumour, when administered alone or together with other agents having anti-tumour properties.

When used to inhibit the formation of insoluble fibrin from fibrin in warm blooded animals, the α-aminoketone derivatives may be administered by intravenous injection or infusion at a daily dose from 2.5mg./kg. to 25mg./kg. given at intervals. Alternatively, the compounds may be administered orally, in which case, a daily dose of from 5mg./kg. to 50mg./kg. is appropriate. In man these doses are equivalent to a total daily dose of from 0.2 to 2.0g. by injection or from 0.4 to 4.0g. given orally. In each case, administration is continued as long as the risk of thrombus formation exists.

The compounds of the invention may be administered in the form of pharmaceutical compositions and according to a further feature of the invention there is provided a pharmaceutical composition comprising an α-aminoketone derivative of the invention or a pharmaceutically-acceptable salt thereof in associated with a pharmaceutically acceptable diluent or carrier.

The composition may be in a form where the α-aminoketone derivative is mixed with one or more diluents, or it may be in a form where the α-aminoketone derivative is enclosed in a carrier, for example a capsule, to give a unit dosage form without the active ingredient being necessarily associated with a diluent.

The composition may be in a form suitable for oral administration, for example a tablet, capsule, solution or suspension, or it may be in a form suitable for parenteral administration, for example a sterile, injectable solution or suspension. Such a composition may be prepared by conventional methods using conventional excipients. A composition for oral administration should preferably contain from 100mg. to 500mg. per dosage unit, and a composition for parenteral administration should preferably contain from 0.5 mg./ml. to 20 mg./ml.; the more dilute compositions being useful for infusion rather than injection.

α-Aminoketone derivatives of formula I wherein $R^1$ is hydrogen are preferably formulated as their pharmaceutically acceptable acid addition salts.

Compositions intended for use in the treatment or maintainance of atherosclerotic disease may also contain one or more other agents which can have a beneficial effect on the disease or on associated conditions, for example ticlopidine, sulfinpyrazone, dipyridamole, clofibrate or acetyl salicylic acid.

The invention is illustrated but in no way limited by the following Examples in which:

(i) N.M.R. spectra were measured using solutions in $d_6$-DMSO with tetramethylsilane as internal standard; (ii) "room temperature" means, at a temperature in the range 18°–27° C.;

(iii) "petrol" means, petroleum either of boiling range 40°–60° C. unless otherwise specified; and (iv) the melting points given for the acid-addition salts below are associated with decomposition.

EXAMPLES 1–10

A mixture of methyl 4-(azidoacetyl)phenoxyacetate (1.5g), N-hydrochloric acid (6ml.), 30% palladium-on-charcoal catalyst (0.1g.) and methanol (100ml.) was shaken in hydrogen at atmospheric pressure until reduction of the carbonyl group began as indicated by a decrease in the total volume of gas (usually about 4 hours). The reaction was then stopped and the reaction mixture filtered. The filtrate was evaporated under reduced pressure, and the residue was recrystallised from a mixture of methanol and diethyl ether to give methyl 4-(aminoacetyl)phenoxyacetate hydrochloride, m.p. 202°–204° C. (Example 1) in 77% yield.

The above process was repeated using an azide of the formula:

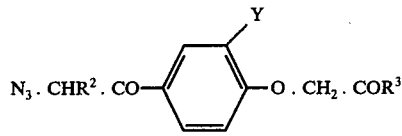

as starting material to give an α-aminoketone of the formula:

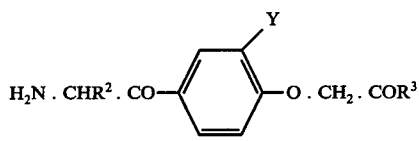

as its hydrochloride.

| Example | $R^2$ | Y | $R^3$ | m.p.(° C.) of hydrochloride | Yield (%) |
|---|---|---|---|---|---|
| 2 | H | H | isopropoxy | 167–170 | 47 |
| 3 | H | H | n-hexyloxy | 122–126 | 65 |
| 4 | H | methoxy | methoxy | 174–175 | 28 |
| 5 | ethyl | H | methoxy | 174–176 | 17 |
| 6 | H | H | morpholino | 174–176 | 68 |
| 7 | H | H | diethylamino | 78–80 | 31 |

-continued

| Example | $R^2$ | Y | $R^3$ | m.p.(° C.) of hydrochloride | Yield (%) |
|---|---|---|---|---|---|
| 8 | H | methoxy | diethylamino | 113–116 | 71 |

In a similar manner using diethyl 4-(azidoacetyl)-phenoxymalonate or methyl 3-(azidoacetyl)phenoxyacetate as starting material, there was obtained diethyl 4-(aminoacetyl)-phenoxymalonate hydrochloride, m.p. 79°–81° C., in 45% yield (Example 9) or methyl 3-(aminoacetyl)phenoxyacetate hydrochloride, m.p. 157° C., in 70% yield (Example 10).

The azides used as starting material were prepared as follows:

A solution of sodium azide (5.4g. 0.08 mol.) in water (30ml.) was added to a solution of an α-haloketone of the formula:

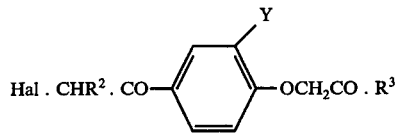

(0.04 mol.) in methylene dichloride (100ml.). Benzyltrimethylammonium chloride (0.1g.) was added, and the biphasic mixture shaken for 16 hours. The organic phase was separated, washed with water (3 × 30ml.), dried and evaporated to give the corresponding azide as a white solid showing the characteristic azide absorption at 2100 cm$^{-1}$ in its infra-red spectrum.

The following azides were obtained:

| $R^2$ | Y | $R^3$ | m.p.(° C.) |
|---|---|---|---|
| H | H | methoxy | 75–78* |
| H | H | isopropoxy | |
| H | H | n-hexyloxy | 66–67 |
| H | methoxy | methoxy | |
| ethyl | H | methoxy | |
| H | H | morpholino | |
| H | H | diethylamino | |
| H | methoxy | diethylamino | |

In each case, the corresponding α-bromoketone was used as starting material except for those compounds marked with an asterisk where the α-chloroketone was used.

In a similar manner using the corresponding α-bromoketone as starting material, diethyl 4-(azidoacetyl)-phenoxymalonate and methyl 3-(azidoacetyl)phenoxyacetate were obtained.

Some of the α-haloketones used to prepare the above azides are new compounds and are obtained as follows:

Isopropyl 4-(bromoacetyl)phenoxyacetate

Potassium carbonate (17.0g.) was added to a solution of isopropyl bromoacetate (24.0g.) and 4-hydroxyacetophenone (17.7g.) in acetone (200ml.). The mixture was heated under reflux for 24 hours, cooled and filtered. The filtrate was evaporated to an oil which was dissolved in ether (150ml.). The solution was washed with sodium bicarbonate solution (2 × 30ml.), water (2 × 30ml.), dried and evaporated. The residual oil was distilled to give isopropyl 4-acetylphenoxyacetate, I.R. peaks at 1750 and 1670 cm$^{-1}$.

Bromine (12g.) was added dropwise to a stirred solution of isopropyl 4-acetylphenoxyacetate (17.6g.) in benzene (200ml.) over 30 minutes. The solution was stirred for a further 15 minutes and then evaporated. The residue was crystallised from ether/hexane to give isopropyl 4-(bromoacetyl)phenoxyacetate, m.p. 60°–61° C.

Methyl 2-methoxy-4-(bromoacetyl)phenoxyacetate

Methyl bromoacetate was reacted with 2-methoxy-4-acetylphenol to give methyl 2-methoxy-4-acetylphenoxyacetate by the same procedure as was used to make isopropyl 4-acetylphenoxyacetate.

Cupric bromide (23.9g.) was then added to a solution of methyl 2-methoxy-4-acetylphenoxyacetate (12.8g.) in a mixture of methyl acetate (150ml.) and chloroform (150ml.). The mixture was stirred and heated under reflux until separation of cuprous bromide was substantially complete. The mixture was cooled and filtered, and the filtrate was washed with brine (3 × 30ml.), dried and evaporated. The residue was chromatographed on silica to give methyl 2-methoxy-4-(bromoacetyl)phenoxyacetate, m.p. 105°–107° C.

n-Hexyl 4-(bromoacetyl)phenoxyacetate

A mixture of 4-acetylphenoxyacetic acid (20.0g.), n-hexanol (10.5g.) and concentrated sulphuric acid (2ml.) in benzene (100ml.) was heated under reflux for 6 hours using a water separator.cThe mixture was then evaporated and the residue dissolved in n-pentane (50ml.). The solution was washed with water (3 × 30ml.) sodium bicarbonate solution (1 × 50ml.) and water again (1 × 50ml.). The solution was evaporated and the residue chromatographed on alumina to give n-hexyl 4-acetylphenoxyacetate, I.R. peaks at 1760 and 1680 cm$^{-1}$.

The n-hexyl 4-acetylphenoxyacetate was then reacted with cupric bromide as described above to give n-hexyl 4-(bromoacetyl)phenoxyacetate, I.R. peaks 1740 and 1690 cm$^{-1}$.

Methyl 4-(2-bromobutyroyl)phenoxyacetate

Methyl bromoacetate was reacted with 4-hydroxybutyrophenone to give methyl 4-butyroylphenoxyacetate, m.p. 78°–82° C. by the procedure described above to make isopropyl 4-acetylphenoxyacetate, and the methyl 4-butyroylphenoxyacetate was reacted with cupric bromide as described above to give methyl 4-(2-bromobutyroyl)phenoxyacetate, I.R. peaks at 1750 and 1680 cm$^{-1}$.

4-[4-(Bromoacetyl)phenoxyacetyl]morpholine

A solution of bromine (8.0g.) in chloroform (30ml.) was added dropwise to a stirred solution of 4-(4-acetylphenoxyacetyl)morpholine (13.15g.) in chloroform (120ml.) at 35° C. After 1 hour, the reaction mixture was filtered and the filtrate was washed with water (2 × 30ml.), dried and evaporated. The residue was recrystallised from methanol/ether to give 4-[4-(bromoacetyl)phenoxyacetyl]morpholine, m.p. 105°–107° C.

N,N-Diethyl-4-(chloroacetyl)phenoxyacetamide

Aluminium chloride (83.3g.) was added in portions over 30 minutes to a rapidly stirred solution of N,N-diethylphenoxyacetamide (51.6g.) and chloroacetyl chloride (31.0g.) in methylene dichloride (200ml.) at 0° C. The mixture was stirred and allowed to reach room temperature over 16 hours. The solvent was evaporated and the residue poured into a mixture of ice (300g.) and concentrated hydrochloric acid (15ml.). The mixture was extracted with methylene dichloride (5 × 100ml.), and the extracts washed with water (2 × 50ml.) dried and evaporated. The residue was chromatographed on alumina to give N,N-diethyl-4-(chloroacetyl)phenoxyacetamide, m.p. 89°–91° C.

N,N-Diethyl-2-methoxy-4-(bromoacetyl)phenoxyacetamide

N,N-Diethyl-2-methoxy4-acetylphenoxyacetamide was reacted with cupric bromide as described above to give N,N-diethyl-2-methoxy-4-(bromoacetyl)phenoxyacetamide, m.p. 101°–103° C.

Diethyl 4-(bromoacetyl)phenoxymalonate

Diethyl bromomalonate was reacted with 4-hydroxyacetophenone to give diethyl 4-acetylphenoxymalonate by the procedure described for the preparation of isopropyl 4-acetylphenoxyacetate.

A solution of bromine (5.4g.) in benzene (50ml.) was added dropwise over 1 hour to a stirred solution of diethyl 4-acetylphenoxymalonate (10.0g.) and t-butyl acetate (3.95g.) in benzene (200ml.). The solution was stirred for 30 minutes, washed with N-sodium bicarbonate solution (1 × 30ml.), water (3 × 40ml.), dried and evaporated. The residue was chromatographed on silica to give diethyl 4-(bromoacetyl)phenoxymalonate, m.p. 55°–58° C.

Methyl 3-(bromoacetyl)phenoxyacetate

Methyl 3-acetylphenoxyacetate was reacted with cupric bromide as described above to give methyl 3-(bromoacetyl)-phenoxyacetate, I.R. peaks at 1745 and 1690 cm$^{-1}$.

EXAMPLE 11

A solution of 4-(bromoacetyl)phenoxyacetic acid (26g.) in chloroform (150ml.) was stirred as hexamine (14g.) was added. The mixture was stirred at room temperature for 3 days and then filtered. The solid was suspended in ethanol (250ml.), concentrated hydrochloric acid (50ml.) was added and the mixture stirred at room temperature for 18 hours. The mixture was then filtered and the filtrate diluted with diethyl ether (1,500ml.). The solid so produced was filtered off, washed with a mixture of ethanol and diethyl ether to give 4-(aminoacetyl)phenoxyacetic acid hydrochloride, m.p. > 250° C. N.m.r. δ 7.0–7.14, 7.92–8.06 each 2H (aromatic protons), 4.5 (2H, N⊕H$_3$CH$_2$CO) and 4.81 (2H, —OCH$_2$.COOH).

EXAMPLE 12–14

Methanol (250ml.) was stirred at −20° C. as thionyl chloride (6ml.) was added. 4-(Aminoacetyl)phenoxyacetic acid hydrochloride (5.0g) was added, and the mixture was stirred and allowed to warm to room temperature during 18 hours. The resulting solution was evaporated under reduced pressure and the residue was recrystallised from a mixture of methanol and diethyl ether to give methyl 4-(aminoacetyl)-phenoxyacetate hydrochloride, m.p. 202°–204° C. (Example 12) in 62% yield.

The above procedure was repeated except that the methanol was replaced by ethanol or n-butanol to give respectively, ethyl 4-(aminoacetyl)phenoxyacetate hydrochloride in 50% yield, m.p. 188°–190° C. (Example 13) or n-butyl 4-(aminoacetyl)phenoxyacetate hydrochloride in 57% yield, m.p. 172°–176° C. (Example 14).

EXAMPLES 15-16

The procedure described in Example 1 was repeated using as starting material ethyl 4-(azidoacetyl)phenylacetate or methyl 3-[4-azidoacetyl)phenyl]propionate to give ethyl 4-(aminoacetyl)phenylacetate hydrochloride in 10% yield, m.p. 183°-185° C. (Example 15) or methyl 3-[4-(aminoacetyl)phenyl]propionate hydrochloride in 21% yield, m.p. 188° C. (Example 16).

The starting azido compounds were prepared as follows:

Ethyl 4-(azidoacetyl)phenylacetate

A solution of sodium azide (32.5g.) in water (200ml.) was added to a solution of ethyl 4-(chloroacetyl)-phenylacetate (24.05g.) in methylene dichloride (200ml.). Benzyltrimethylammonium chloride (0.1g.) was added, and the bisphasic mixture was shaken for 4 hours at room temperature. The organic phase was separated, washed with distilled water (3 × 30ml.) dried and evaporated to give ethyl 4-(azidoacetyl)-phenylacetate as an oil showing a peak at 2120 cm$^{-1}$ in its I.R. spectrum.

Methyl 3-[4-(azidoacetyl)phenyl]propionate

A solution of methyl 3-[4-(chloroacetyl)phenyl]-propionate was reacted with sodium azide as described above for ethyl 4-(chloroacetyl)phenylacetate to give an oil showing a peak of 2120 cm$^{-1}$ in its I.R. spectrum.

The methyl 3-[4-(chloroacetyl)phenyl]propionate was obtained as follows:

A mixture of 3-phenylpropionic acid (50g.), methanol (250ml.) and concentrated sulphuric acid (12ml.) was heated under reflux for 12 hours, and then the excess of methanol was evaporated under reduced pressure. The residue was added to saturated aqueous sodium bicarbonate solution (100ml.) containing ice (400g.) and the pH adjusted to 9 by the addition of more sodium bicarbonate solution. The mixture was extracted with ether (5 × 100ml.), and the extracts combined, washed with brine (2 × 50ml.), dried and evaporated to give methyl 3-phenylpropionate as an oil with a peak at 1740 cm$^{-1}$ in its I.R. spectrum.

Aluminum chloride (225g.) was added to a rapidly stirred mixtures of the above ester (41g.) and chloroacetyl chloride (113g.) in carbon disulphide at 0° C. The stirred mixture was allowed to warm to room temperature during 2 hours, and the carbon disulphide then evaporated. The residue was added to a mixture of ice (500g.) and concentrated hydrochloric acid (15ml.), and the mixture extracted with methyl acetate (4 × 200ml.) and then methylene dichloride (2 × 150ml.). The extracts were combined, washed with brine (2 × 100ml.), dried and evaporated to a residue which was crystallised from a 2:1 mixture of diethyl ether and n-pentane to give methyl 3-[4-(chloroacetyl)phenyl]propionate, m.p. 90° C.

EXAMPLES 17-21

Using a similar procedure to that described in Example 1 but using an azide of the formula:

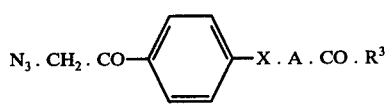

XV as starting material there was obtained an α-aminoketone of the formula:

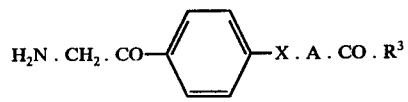

XVI as its hydrochloride in a yield of 35-75%.

| Ex. | X | A | R$^3$ | m.p. (° C.) of hydrochloride |
|---|---|---|---|---|
| 17 | CH$_2$ | —CH$_2$— | OH | 208 |
| 18 | O | —CMe$_2$— | OEt | 108-109 |
| 19 | O | —CHMe— | OEt | * |
| 20 | O | —(CH$_2$)$_3$— | OMe | 165-169 |
| 21 | CH$_2$ | —CH$_2$— | —NH . CHMe . CO$_2$Me | 187-190 |

*microanalysis found: C, 53.1, H, 6.2; N, 4.8; C$_{13}$H$_{17}$NO$_4$ . HCl . ¼ H$_2$O requires: C, 53.4; H, 6.3; N, 4.8

The following azides of formula XV used as starting materials, were prepared using the procedure described in Example 1 and had the characteristic azide absorption at 2100 cm$^{-1}$ in their respective infra-red spectrum:

| Starting material for Example | X | A | R$^3$ |
|---|---|---|---|
| 18 * | O | —CMe$_2$— | OEt |
| 19 | O | —CHMe— | OEt |
| 20 | O | —(CH$_2$)$_3$— | OMe |
| 21 | CH$_2$ | —CH$_2$— | —NH . CHMe . CO$_2$Me |

In each case the corresponding α-chloroketone was used as starting material, except where marked with an asterisk where the α-bromoketone was used. 3-[4-(Azidoacetyl)phenyl]propionic acid was prepared as follows:

A solution of sodium azide (2.0g.) in water (20ml.) was added to a stirred suspension of 3-[4-(chloroacetyl)phenyl]-propionic acid (5g.) in water (30ml.). After stirring for 16 hours at room temperature, the residual solid was separated, washed with cold water (2 × 10ml.) and dried in vacuo to give 3-[4-(azidoacetyl)phenyl]propionic acid as a white solid, which possessed a characteristic azide absorption in the infra-red spectrum at 2120 cm$^{-1}$.

The following α-haloketones used to prepare the above azides are new compounds and were obtained as follows:

3-[4-(chloroacetyl)phenyl]propionic acid

A solution of 3-phenylpropionic acid (50g.) in ethylenedichloride (200ml.) was added over 1 hour to a stirred mixture of chloroacetyl chloride (37.7g.) and aluminum chloride (48.9g.) in ethylene dichloride (550ml.) at room temperature. The resulting mixture was stirred for 1 hour and was then poured cautiously onto a mixture of ice (2kg.) and concentrated hydrochloric acid (50ml.). After stirring for a further 16 hours, the crude product was separated by filtration and recrystallised from water to give 3-[4-(chloroacetyl)phenyl]propionic acid, m.p. 151°-153° C.

Ethyl 2-[4-(bromoacetyl)phenoxy]-2-methylpropionate

Ethyl 2-[4-acetylphenoxy]-2-methylpropionate was brominated using an analogous procedure to that described for 4-[4-(bromoacetyl)phenoxyacetyl]morpholine, used as a starting material for Example 6, to give ethyl 2-[4-(bromoacetyl)phenoxy]-2-methylpropionate as an oil, which was pure by thin layer chromatographic (TLC) analysis (on silica plates; eluant : 50% ether/50% petrol).

Ethyl 2-[4-(chloroacetyl)phenoxy]propionate

Ethyl 2-phenoxypropionate was reacted with chloroacetyl chloride as described for N,N-diethyl-4-(chloroacetyl)phenoxyacetamide, used as a starting material for Example 7, to give ethyl 2-[4-(chloroacetyl)phenoxy]-propionate as a white solid, having a satisfactory analysis (found: C, 57.7, H, 5.5, N, 13.0; required: C, 57.7; H, 5.6; N, 13.1).

Methyl 4-[4-(chloroacetyl)phenoxy]butyrate

Methyl 4-phenoxybutyrate was reacted with acetyl chloride in a similar manner to that described above for 3-[4-(chloroacetyl)phenyl]propionic acid, except that the crude product was triturated with petrol to give methyl 4-[4-(chloroacetyl)phenoxy]butyrate as a crystalline solid which was pure by TLC analysis (on silica plates; eluant: 50% ether/50% petrol).

N-{3-[4-(Chloroacetyl)phenyl]propionyl}alanine methyl ester

A solution of pivaloyl chloride (4.41ml.) in tetrahydrofuran (30ml.) was added to a stirred solution, cooled to −15° C., of 3-[4-(chloroacetyl)phenyl]propionic acid (9.7g.) and triethylamine (5.5ml.) in tetrahydrofuran (30ml.) and acetonitrile (40ml.). The resultant mixture was stirred for one hour at −15° C. A suspension of DL-alanine methyl ester hydrochloride (5.0g.) in dimethylformamide (30ml.) containing triethylamine (5.5ml.) was then added over 15 minutes. The mixture was stirred at −15° C. for 1 hour and then for 16 hours at room temperature. Saturated sodium bicarbonate solution (30ml.) was added and the solution was stirred for 30 minutes and then evaporated in vacuo. The residue was mixed with water (150ml.) and was extracted with chloroform (2 × 100ml.). The extracts were washed successively with 10% hydrochloric acid (200ml.), water (200ml.), saturated sodium bicarbonate solution (200ml.) and water (200ml.), dried (MgSO$_4$) and evaporated. The residue was recrystallised from toluene/petrol to give N-{3-[4-(chloroacetyl)phenyl]-propionyl} alanine methyl ester, m.p. 122°–124° C.

EXAMPLE 22

The procedure described in Example 12 was repeated, except that the methanol was replaced by n-propyl alcohol. There was thus obtained n-propyl-4-(aminoacetyl)-phenylacetate hydrochloride m.p. 194°–197° C. in 55% yield.

EXAMPLES 23–24

Concentrated hydrochloric acid (20ml.) was added dropwise to a stirred suspension of methyl 4-(azidoacetyl)-phenoxyacetate (5g.) and zinc dust (1g.) in methanol (100ml.) at such a rate as to maintain evolution of hydrogen and until TLC analysis (on silica plates;eluant, 1:4 v/v methanol/chloroform) showed disappearance of the starting azide. The mixture was then filtered and evaporated in vacuo. The resultant residue was dissolved in water (45ml.) and the solution obtained was washed first with chloroform (30ml.) and then with ether (30ml.). The aqueous phase was evaporated in vacuo to give a solid residue which was recrystallised from methanol. There was thus obtained the zinc chloride complex of methyl 4-(aminoacetyl)phenoxyacetate hydrochloride (Example 23) (2.5g.), m.p. 137°–140° C.

In a similar manner, but starting from methyl 4-(azidoacetyl)thiophenoxyacetate (10g.), there was obtained the zinc chloride complex of methyl 4-(aminoacetyl)-thiophenoxyacetate hydrochloride (Example 24) (3.9g.) m.p. 167°–170° C.

The methyl 4-(azidoacetyl)thiophenoxyacetate starting material was obtained as follows:

A solution of methyl thiophenoxyacetate (60g.) in methylene chloride (100ml.) was added over 20 minutes to a stirred suspension of chloroacetyl chloride (45.2g.) and aluminium chloride (134g.) in methylene chloride (400ml.) at room temperature. The resulting solution was stirred at room temperature overnight and poured onto a mixture of ice (2kg.) and concentrated hydrochloric acid (50ml.). This mixture was then stirred at room temperature for 1 hour. The methylene chloride phase was separated, dried (MgSO$_4$) and evaporated in vacuo. The residue was recrystallised from methanol to give methyl 4-(chloroacetyl)-thiophenoxyacetate (60.1g.), m.p. 61°–63° C.

A solution of sodium azide (17.0g.) in water (100ml.) was added to a solution of methyl 4-(chloroacetyl)thiophenoxyacetate (60.1g.) in chloroform (350ml.). Benzyl triethylammonium chloride (300mg.) was then added, and the two phase mixture was shaken for 16 hours. The organic phase was separated, washed with water (2 × 100ml.), dried (MgSO$_4$) and then evaporated in vacuo. The residue was recrystallised from methanol to give methyl 4-(azidoacetyl)thiophenoxyacetate (49.3g.), having a characteristic azide absorption at 2110cm$^{-1}$ in the infra-red spectrum.

EXAMPLE 25

Pyridine (40ml.) was added to a stirred mixture of methyl 4-(aminoacetyl)phenoxyacetate hydrochloride (5.2g.) and ethyl chloroformate (2.3g.). An exothermic reaction occurred and was allowed to continue until a homogeneous solution was obtained. This solution was then cooled and the solid residue which formed was first separated, and then washed successively with ether (2 × 30ml.), water (2 × 30ml.) and ether (2 × 30ml.), before recrystallisation from toluene to give methyl 4-[N-(ethoxycarbonyl)aminoacetyl]-phenoxyacetate (4.7g.), m.p. 128°–129° C.

EXAMPLE 26

A solution of ethyl 2-[4-(aminoacetyl)phenoxy]-2-methylpropionate hydrochloride (4g.) in 2N hydrochloric acid (16ml.) and dioxan (60 ml.) was stirred and heated under reflux for 24 hours. The solution was then evaporated in vacuo and the residue dissolved in ethanol. The solution obtained was decolourised with carbon and evaporated in vacuo to give a residue which crystallised on being triturated with a mixture of ether, ethyl acetate and acetone (4:1:1 v/v) to give 2-[4-aminoacetyl)phenoxy]-2-methylpropionic acid hydrochloride (2.55g.), m.p. 188°–190° C.

EXAMPLE 27

A solution of ethyl 2-[4-(aminoacetyl)phenoxy]-propionate hydrochloride (2.0g.) in a mixture of methanol (150ml.) and a saturated solution of hydrogen chloride in ether (1ml.) was stirred and heated under reflux for 48 hours. The reaction mixture was then evaporated in vacuo and the residue was triturated with ether (50ml.) (dried over sodium wire) to give methyl 2-[4-

(aminoacetyl)phenoxy]propionate hydrochloride which was isolated as a hygroscopic solid (1.3g.) having a satisfactory analysis; found: C, 50.0%; H, 5.9%, N, 4.9%; required (+ ¾ mole $H_2O$): C, 50.2%; H, 6.1%; N, 4.9%.

EXAMPLE 28

A mixture of 4-methoxycarbonyl-5-[4-(methoxycarbonylmethoxy)phenyl]oxazole (2.34g.) and a saturated solution of hydrogen chloride in methanol (20ml.) was heated under reflux for 2 hours. The reaction mixture was then evaporated in vacuo and the yellow residue obtained was triturated with ether (100ml.) (dried over sodium wire) to give methyl 4-(α-amino-α-methoxycarbonylacetyl)phenoxyacetate hydrochloride as an off-white amorphous solid (1.9g.), m.p. 120°-125° C., having a satisfactory analysis; found: C, 48.9%; H, 5.1%; N, 4.2%; required: C, 49.2%; H, 5.05%; N, 4.42%.

The substituted oxazole starting material was obtained as follows:

A mixture of benzyl 4-hydroxybenzoate (169.0g.), methyl bromoacetate (122.4g.) and anhydrous potassium carbonate (200g.) in acetone (500ml.) (analytical grade) was stirred and heated under reflux for 16 hours. The mixture was then filtered and the filtrate evaporated in vacuo. The semi-solid residue obtained was separated by filtration. The solid thus obtained was washed with cold (0°-5° C.) petroleum ether (b.p. 60°-80° C.) (50ml.) to give benzyl 4-(methoxycarbonylmethoxy)benzoate, m.p. 63°-66° C.

A solution of the thus obtained benzoate (65g.) in methanol (100ml.) was mixed with 30% w/w palladium-on-carbon catalyst (1.0g.) and hydrogenated during 6 hours. After removal of catalyst by filtration, the reaction solution was evaporated in vacuo to leave an oil which crystallised slowly. The solid thus formed was recrystallised from methanol to give 4-(methoxycarbonylmethoxy)benzoic acid, m.p. 164°-165° C.

A suspension of the thus obtained benzoic acid (12.2g.) in toluene (100ml.) (dried over sodium wire) was treated with oxalyl chloride (19.05g.) and the mixture was stirred for 1.5 hours. The homogeneous solution which had formed was then evaporated to give 4-(methoxycarbonylmethoxy)-benzoyl chloride as a solid of low melting point, having characteristic carbonyl absorptions in the infra-red spectrum at 1770 and 1750 $cm^{-1}$.

The above substituted benzoyl chloride (12.6g.) was dissolved in tetrahydrofuran (100ml.). To this solution was added a mixture of methyl isocyanoacetate (6.0g.) and triethylamine (25.2ml.). After being stirred at room temperature for 24 hours the reaction mixture was cooled to 0°-5° C. The solid thus formed was separated by filtration to give 4-methoxycarbonyl-5-[4-(methoxycarbonylmethoxy)phenyl]oxazole, m.p. 120°-125° C. (decomposition).

EXAMPLE 29

In a similar manner to that described in Example 1, but replacing the N-hydrochloric acid (6ml.) by one equivalent of citric, lactic or sulphuric acid respectively there were obtained in essentially quantitative yield the following salts of methyl 4-(aminoacetyl)phenoxyacetate:
citrate, m.p. 135°-136° C.
lactate, m.p. 128°-131° C.
sulphate, m.p. 125°-128° C.

EXAMPLE 30

A solution of acetic anhydride (7.0ml.) and formic acid (3.0ml.) was stirred at 60° C. for 2 hours. Methyl 4-(aminoacetyl)thiophenoxyacetate hydrochloride zinc chloride complex (2.5g.) was then added at room temperature and the mixture was stirred at that temperature for 1 hour. After the addition of tetrahydrofuran (30ml.) the mixture was further stirred at room temperature for 48 hours and then evaporated in vacuo. The residue thus obtained was extracted with chloroform (100ml.) and the extracts washed first with 1N hydrochloric acid (30ml.) and then with water (50ml.), dried ($MgSO_4$) and evaporated. The residue obtained was recrystallised from a mixture of toluene and petrol to give methyl 4-[N-(formyl)amino-acetyl]-thiophenoxyacetate (1.0g.) m.p. 65°-66° C.

EXAMPLE 31

A mixture of methyl 4-(aminoacetyl)phenoxyacetate hydrochloride (2.6g.) and trimethyl orthoformate (3.18g.) was stirred at 100° C. for 1 hour under reflux. The volatile reaction products were then allowed to distil off. The yellow residual oil thus obtain crystallised on cooling to give methyl 4-[(N-formyl)aminoacetyl]-phenoxyacetate as a solid (2.2g.), m.p. 116° C., after recrystallisation from methanol.

EXAMPLE 32

A solution of methyl 4-[N-(formyl)aminoacetyl]-thiophenoxyacetate (3.0g.) and sodium metaperiodate (2.4g.) in a mixture of methanol and water (6:1 v/v)(350ml.) was stirred at room temperature for 48 hours. The solid residue was separated by filtration and the filtrate evaporated in vacuo to give a solid which was dissolved in chloroform (50ml.). The solution obtained was washed with water (50ml.), dried ($MgSO_4$) and evaporated in vacuo to give a residue which was triturated with a mixture of acetone and ether (1:1 v/v). There was thus obtained methyl 4-[(N-formyl)aminoacetyl]phenylsulphinylacetate (1.7g.), m.p. 125°-127° C.

EXAMPLES 33-34

A mixture of methyl 4-[N-(formyl)aminoacetyl]-thiophenoxyacetate (10.1g.) and a saturated solution of hydrogen chloride in methanol (100ml.) was left at room temperature for 4 days. The mixture was then evaporated in vacuo and the residue recrystallised from a mixture of ether and methanol to give methyl 4-(aminoacetyl)thiophenoxyacetate hydrochloride (Example 33) (9.5g.), m.p. 161°-165° C. (decomposition, monohydrate).

In a similar manner methyl 4-(aminoacetyl)phenoxyacetate hydrochloride (Example 34), m.p. 202°-204° C. may be obtained from methyl 4-[N-(formyl)aminoacetyl]phenoxyacetate, in essentially quantitative yield.

EXAMPLE 35

A mixture of methyl 4-(nitroacetyl)phenoxy acetate (220 mg.), 30% w/w palladium-on-charcoal (20mg.), N-HCL (1ml.), dioxan (50ml.) and methanol (20ml.) was shaken at room temperature in an atmosphere of hydrogen, until the theoretical amount of hydrogen had been absorbed. The mixture was then filtered and the solvents removed in vacuo. The residue was dissolved in water (20ml.) and washed with methyl acetate (20ml.), the aqueous phase was evaporated in vacuo and the residue was recrystallised from methanol and ether to give methyl 4-(aminoacetyl)phenoxyacetate hydrochloride (100mg.), m.p. 202°-204° C.

The methyl (4-nitroacetyl)phenoxyacetate starting material was prepared by the following procedure:

Methyl 4-(iodoacetyl)phenoxy acetate (2.0g.) was added to a stirred suspension of silver nitrite (2.5g.) in ether (150ml.) (dried over sodium wire) at −10° C. The mixture was stirred at room temperature for 48 hours and the ether decanted off. The solid residue was then extracted with methyl acetate and the extracts evaporated in vacuo. The residue was recrystallised from methanol to give methyl 4-(nitroacetyl)phenoxy acetate, m.p. 142°-143° C.

Methyl (4-iodoacetyl)phenoxy acetate was itself prepared as follows:

A suspension of methyl 4-(chloroacetyl)phenoxy acetate (10.0g.), and sodium iodide (12.4g.) in acetone (200ml.) (analytical grade) was stirred overnight at room temperature. The solids were removed by filtration and the filtrate thus obtained was evaporated in vacuo to give methyl 4-(iodoacetyl)-phenoxy acetate, m.p. 81°-83° C.

EXAMPLE 36

Methyl 4-(azidoacetyl)phenoxyacetate (2.49g.) was added to a stirred solution of triphenylphosphine (2.62g.) in tetrahydrofuran (20ml.) maintained at 40° C. The solution gradually became orange during the addition of the azido compound and was further stirred at 40° C. for 15 minutes after the addition was complete. 1N-Hydrochloric acid (20ml.) was then added and the mixture stirred at 40° C. for 15 minutes. The mixture was cooled to room temperature and then ether (200ml.) was added. The ethereal layer was decanted off and the brown oily residue was dissolved in toluene (20ml.) and the solution obtained was evaporated in vacuo. The solid residue formed was then recrystallised twice from methanol to give methyl 4-(aminoacetyl)-phenoxyacetate hydrochloride (0.7g.), m.p. 202°-204° C.

EXAMPLE 37

A mixture of micro-crystalline cellulose (196 parts by weight) and methyl 4-(aminoacetyl)phenoxyacetate hydrochloride (200 parts by weight) was sieved through a 30 mesh screen. Magnesium stearate (60 mesh particle size) (4 parts by weight) was added and, after thorough mixing, the resultant mass was compressed into tablets.

There were thus obtained tablets, each weighing 400mg. and containing 200mg. of active ingredient, which may be administered to man for therapeutic purposes.

In a similar manner, tablets containing 300mg., 400mg. or 500mg. of active ingredient may be obtained.

The above active ingredient may be replaced by any compound of formula I or a pharmaceutically acceptable acid addition salt thereof, described in any of Examples 1-36.

EXAMPLE 38

Methyl 4-(aminoacetyl)phenoxyacetate hydrochloride was charged into soft gelatin capsules so that individual capsules contained 250mg. or 500mg. of active ingredient. The filled capsules obtained may be administered to man for therapeutic purposes.

The above active ingredient may be replaced by any compound of formula I or a pharmaceutically acceptable acid addition salt thereof described in any of Examples 1-36 and may, if desired, also include an inert, pharmaceutically acceptable diluent or carrier.

What we claim is:

1. An α-aminoketone derivative of the formula:

$$R^1NH.CHR^2.CO.Ar.X.A.CO.R^3 \qquad I$$

wherein $R^1$ is hydrogen; $R^2$ is hydrogen; $R^3$ is a hydroxy or $C_{1-8}$-alkoxy radical; and wherein Ar is a p-phenylene radical; X is oxygen; and A is a methylene radical; or a pharmaceutically acceptable acid addition salt or a metal complex thereof of an α-aminoketone derivative of formula I wherein $R^1$ is hydrogen; or a pharmaceutically-acceptable base addition salt of an α-aminoketone derivative of formula I wherein $R^3$ is a hydroxy radical.

2. An α-aminoketone derivative as claimed in claim 1 wherein $R^3$ is a hydroxy or methoxy.

3. 4-(Aminoacetyl)phenoxyacetic acid or methyl 4-(aminoacetyl)phenoxy acetate; or a pharmaceutically acceptable salt thereof.

4. An α-aminoketone derivative as claimed in claim 1 which is in the form of its hydrohalide, sulphate, phosphate or 2-hydroxyethylsulphonate salt, or its salt with a carboxylic acid.

5. A pharmaceutical composition for use in inhibiting the formation of thrombi and in reducing the persistence of thrombi formed in the blood of warm blooded animals, said composition containing an effective amount of an α-aminoketone derivative according to claim 1, in association with a pharmaceutically acceptable diluent or carrier.

6. A method for inhibiting the formation of insoluble fibrin from fibrin in warm blooded animals which comprises administering to said animals an effective amount of a composition as claimed in claim 5.

7. An α-aminoketone derivative as claimed in claim 1, said derivative being methyl 4-(aminoacetyl) phenoxyacetate.

* * * * *